US007132285B2

(12) United States Patent
Bolton et al.

(10) Patent No.: US 7,132,285 B2
(45) Date of Patent: Nov. 7, 2006

(54) APOPTOTIC ENTITIES FOR USE IN TREATMENT OF NEURODEGENERATIVE AND OTHER NEUROLOGICAL DISORDERS

(75) Inventors: Anthony E. Bolton, Tideswell (GB); Arkady Mandel, North York (CA); Daniel Sauder, Toronto (CA)

(73) Assignee: Vasogen Ireland Limited (IE)

( * ) Notice: Subject to any disclaimer, the term of this patent is extended or adjusted under 35 U.S.C. 154(b) by 207 days.

(21) Appl. No.: 09/871,146

(22) Filed: May 25, 2001

(65) Prior Publication Data

US 2002/0044924 A1 Apr. 18, 2002

(30) Foreign Application Priority Data

May 25, 2000 (CA) .................................. 2309424

(51) Int. Cl.
  C12N 5/08 (2006.01)
  C12N 5/00 (2006.01)
  C12N 15/01 (2006.01)
  A01N 63/00 (2006.01)
  A01N 65/00 (2006.01)

(52) U.S. Cl. ...................... 435/372; 435/375; 435/325; 435/366; 435/448; 435/173.7; 424/93.7; 424/93.1

(58) Field of Classification Search ............... 424/93.7, 424/93.71, 93.1, 93.21; 435/325, 366
See application file for complete search history.

(56) References Cited

U.S. PATENT DOCUMENTS

| 2002/0051771 | A1 | 5/2002 | Bolton, et al. |
| 2002/0058023 | A1 | 5/2002 | Bolton, et al. |
| 2003/0139466 | A1 | 7/2003 | Peritt et al. |
| 2003/0157073 | A1 | 8/2003 | Peritt et al. |

FOREIGN PATENT DOCUMENTS

| WO | 93/15779 | 8/1993 |
| WO | WO 98/07436 | 2/1998 |
| WO | 00/41705 | 7/2000 |
| WO | 01/66875 | 9/2001 |
| WO | WO 03/045979 | 6/2003 |

OTHER PUBLICATIONS

Herrmann et al., 1998, Arthritis &Rheumatism, vol. 41, No. 7, pp. 1241-1250.*
Bartholeyns et al, 1998, Res.Immunol., 149, pp. 647-649.*
Bliss, T.V.P., et al., "A synaptic model of memory: long-term potentiation in the hippocampus," *Nature*, 361:31-39 (1993).
Bombeli, T., et al., "Apoptotic Vascular Endothlial Cells Become Procoagulant," *Blood*, 89:2429-2442 (1997).
Buttke and Sandstrom, et al., "Oxidative Stress As a Mediator of Apoptosis," *Immunology Today*, 15:7-10 (1994).

Fadok, V.A., et al., "Exposure of Phosphatidylserine on the Surface of Apoptotic Lymphocytes Triggers Specific Recognition and Removal by Macrophages," *Journal of Immunology*, 148:2207-2216 (1992).
Fadok, V. A., et al., "A receptor for Phosphatidylserine-specific clearance of apoptotic cells," *Nature*, 405:85-90 (2000).
Gavrieli, Y., et al., "Identification of Programmed Cell Death In Situ via Specific Labelling of Nuclear DNA Fragmentation," *J. of Cell Biology*, 119:493-501 (1992).
Griffin, W.S.T., et al., "Brain interleukin 1 and S-100 immunoreactivity are elevated in Down Syndrome and Alzheimer disease," *Proceedings of the National Academy of Sciences USA*, 86:7611-7615 (1989).
Guijarro, C., et al., "3-Hydrxy-3 Methylglutaryl Coenzyme A Reductase and Isoprenylation Inhibitors Induce Apoptosis of Vascular Smooth Muscle in Culture," *Circulation Research*, 83:490-500 (1998).
Kerr, et al., "Apoptosis: A basic biological phenomenon with wide-ranging implications in tissue kinetics," *British Journal of Cancer*, 26:239-257 (1991).
Kondo, et al., "Lymphocyte Function-Associated Antigen-1 is Required for Maximum Elicitation of Allergic Contact Dermatitis," *Br. J. Dermatol.* 131:354-359 (1994).
Kondo, et al., "Interleukin-10 Inhibits the Elicitation Phase of Allergic Contact Hypersensitity," *The Journal of Investigative Dermatology*, 103:811-814 (1994).
Loo, D. T. and Rillema, J.R., "Measurement of Cell Death," *Methods in Cell Biology*, 57:251-264 (1998).
Mogi, M., et al., "Interleukin (IL)-1 beta, IL-1, IL-4 , , , IL-6 and transforming growth factor-alpha levels are elevated in ventricular cerebrospinal fluid in juvenile parkinsonism and Parkinson's disease," *Neuroscience Letters*, 211:13-16 (1996).
Murray, C.A., et al., "Evidence that increase hippocampal expression of the cytokine interleukin-1β is a common trigger for age and stress-induced impairments in long-term potentiation," *Journal of Neuroscience*, 18:2974-2981 (1998).
Salvioli, S., et al., "JC-1, but not $DiOC_6(3)$ or Rhodamine 123, is a Reliable Fluorescent Probe to Assess $\Delta\psi$ Changes in Intact Dells: Implications For Studies on Mitochondrial Functionality During Apoptosis," *FEBS Letters*, 411:77-82 (1997).
Susin, S.A., "Mitochondrial Release of Caspase-2 and -9 During the Apoptotic Process," *Journal of Experimental Medicine*, 189:381-394 (1994).
Suzuki, Y., "Cell Death Phagocytosis, and Neurogenesis in Mouse Olfactory Epithelium and Vomeronasal Organ After Colcicine Treatment," *Annals of the New York Academy of Sciences*, 855:252-254 (1998).
Teiger, E., "Apoptosis in Pressure Overload-Induced Heart Hypertrophy in the Rat," *Journal of Clinical Investigation*, 97:2891-2897 (1996).

(Continued)

*Primary Examiner*—Olga N. Chernyshev
(74) *Attorney, Agent, or Firm*—Foley & Lardner LLP

(57) ABSTRACT

Treatment and/or prophylaxis, in mammalian patients, of neurodegenerative and other neurological medical disorders is effected by administering to the patient effective amounts of apoptotic bodies and/or apoptotic cells, preferably those derived from the patient's own white blood cells, e.g. by extracorporeal treatment of the patient's blood cells to induce apoptosis and administration of the apoptotic bodies and/or cells so formed to the patient.

4 Claims, 1 Drawing Sheet

OTHER PUBLICATIONS

Bodey, B., et al. "Apoptosis in the Mammalian Thymus During Normal Histogenesis and under Various *in Vitro* and *in Vivo* Experimental Conditions." *In Vivo.* 12: 123:134 (1998).

Shivji, G.M., et al. "Effects of VAS972 therapy on Ellerigc Contact Hypersensitivity." *J. Invest. Dermatol.* New York, NY. 114(4): 862 (2000). (Abstract).

Marina, et al. "Apoptosis of Human Lymphocytes in the Absence or Presence of Internucleosomal DNA Cleavage" *Biochemical and Biophysical Research Communications* 229:910-915 (1996).

Shivji, et al., The Effect of VAS972 on Allergic Contact Hypersensitivity, Journal of Cutaneous Medicine and Surgery, vol. 4, No. 3, 2000, pp. 132-138.

Bolton, "Biological Effects and Basic Science of a Novel Immune-Modulation Therapy," *Amer. J. Cardiol.* 95(11A):24C-29C (Jun. 6, 2005).

Maeda, et al., "Intravenous infusion of syngeneic apoptotic cells by photophoresis induces antigen-specifi regulatory T cells." *J. Immunol.* 174(10):5968-5976 (May 15, 2005).

\* cited by examiner

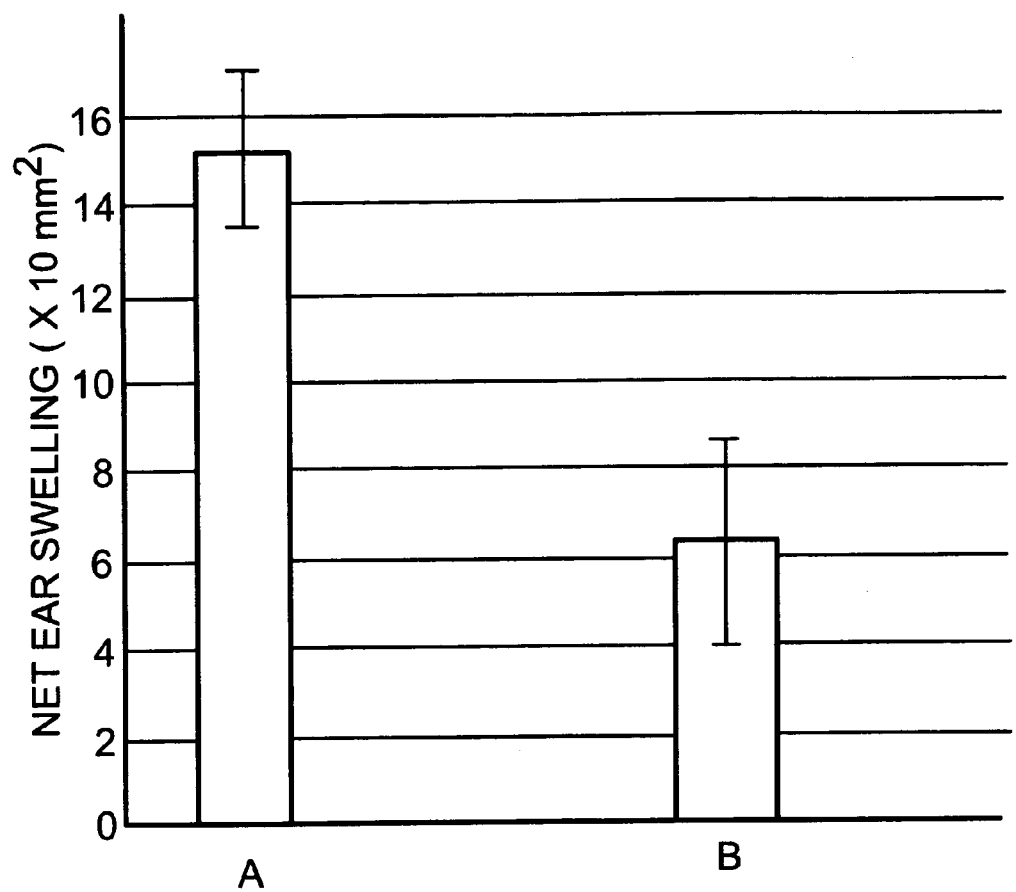
Figure

APOPTOTIC ENTITIES FOR USE IN TREATMENT OF NEURODEGENERATIVE AND OTHER NEUROLOGICAL DISORDERS

FIELD OF THE INVENTION

This invention relates to biochemical and biological compositions and to the uses thereof in the treatment and/or prophylaxis of various neurodegenerative and other neurological disorders in mammalian patients. More particularly, it relates to treatment and prophylaxis of neurodegenerative and other neurological disorders by administration of compositions containing the mammalian cellular materials and fragments thereof, and to the compositions containing the mammalian cellular materials and fragments themselves, and to processes for preparing such compositions.

BACKGROUND OF THE INVENTION

Two mechanisms of cell death in the body are recognized, necrosis and apoptosis. Apoptosis is the process of programmed cell death, described by Kerr et al in 1992 [Kerr JFR, Wyllie AH, Currie AR (1992). "Apoptosis: a basic biological phenomenon with wide-ranging implications in tissue kinetics. "British Journal of Cancer 26: 239–257"], by which steady-state levels of the various organ systems and tissues in the body are maintained as continuous cell division and differentiation takes place. Cells undergoing apoptosis often exhibit distinctive morphological changes such as a pronounced decrease in cell volume, modification of the cytoskeletons resulting in pronounced membrane blebbing, a condensation of the chromatin, and degradation of the DNA into oligonucleosomal fragments. Following these morphological changes, an apoptotic cell may break up into a number of small fragments known as apoptotic bodies, consisting essentially of membrane-bound bodies containing intact organelles, chromatin, etc. Apoptotic bodies are normally rapidly removed from the body by phagocytosis by macrophages, dendritic cells and other antigen presenting cells, before they can become lysed and release their potentially pro-inflammatory intracellular contents.

In simple outline, apoptosis is thought to proceed as follows. Three phases can be identified in the apoptotic mechanism of programmed cell death:
Induction phase;
Effector phase; and
Degradation phase.

The induction phase is dependent, in part, on specific interactions of death-inducing signals at the cell surface membrane. One common signal is initiated by the binding of specific ligands to receptors of the TNF receptor family present on the cell membrane. One important such receptor is Fas (APO-1, CD95), which interacts with Fas-ligand to initiate apoptosis.

The effector phase, activated by the binding of receptors and ligands of the induction phase, leads to the activation of caspases, cystinyl-aspartate-requiring proteinases (proteolytic enzymes), including caspases 1 and 8. This activation may be associated with a change in the permeability of mitochondria, allowing the release of cytochrome-c which is involved in caspase activation. Activated caspases initiate a chain of lethal proteolytic events culminating in the changes in chromatin and cytoskeletal components seen in apoptosis.

Many cells undergoing apoptosis can be identified by a characteristic 'laddering' of DNA seen on agarose gel electrophoresis, resulting from cleavage of DNA into a series of fragments. These changes occur a few hours before death of the cell as defined by the ability of a cell to exclude vital dyes. The appearance of DNA laddering on agarose gel electrophoresis following extraction of DNA from cells is one recognised method of identification of apoptosis in cells [Loo, D. T. and Rillema, J. R. (1998) "Measurement of Cell Death," Methods in Cell Biology 57: 25 1–264], although it is not always sensitive enough to detect apoptosis. In situ labelling of nuclear DNA fragmentation, for example, using commercially available terminal dUTP nick end labelling (TUNEL) assays, is an alternative and more reproducible measure for the determination of fragmented DNA in apoptotic cells and cells undergoing apoptosis [Gavrieli Y, Sherman Y, Ben-Sasson S A (1992)", "Identification of programmed cell death in situ via specific labelling of nuclear DNA fragmentation". Journal of Cell Biology 119: 493–501].

During apoptosis, phosphatidylserine becomes exposed externally on the cell membrane [Fadok V A, Voelker D R, Campbell P A, Cohen J J, Bratton D L, Henson P M (1992), "Exposure of phosphatidylserine on the surface of apoptotic lymphocytes triggers specific recognition and removal by macrophages". Journal of Immunology 148: 2207–2216] and this exposed phosphatidylserine binds to specific receptors to mediate the uptake and clearance of apoptotic cells in mammals [Fadok V A, Bratton D L, Rose D M, Pearson A, Ezekewitz R A B, Henson P M (2000), "A receptor for phosphatidylserine-specific clearance of apoptotic cells", Nature 405: 85–90]. The surface expression of phosphatidylserine on cells is another recognised method of identification of apoptotic cells.

Changes in mitochondrial integrity are intimately associated with apoptosis, resulting in alterations in mitochondrial membrane permeability and the release of cytochrome-c from the mitochondria into the cell cytoplasm [Susin, S. A., Lorenzo, H. K., Zamzami, N., Marzo, I, Brenner, C., Larochette, N., Prevost, M. C., Alzari, P. M. and Kroemer, G. (1999) "Mitochondrial Release of Caspase-2 and -9 during the Apoptotic Process", Journal of Experimental Medicine, 189: 381–394]. Measurement of changes in mitochondrial membrane potential, reflecting changes in mitochondrial membrane permeability, is another recognised method of identification of apoptotic cells.

A number of other methods of identification of cells undergoing apoptosis and of apoptotic cells, many using monoclonal antibodies against specific markers for apoptotic cells, have also been described in the scientific literature.

Necrosis, in contrast, is cell death of a pathological nature, resulting from injury, bacterial toxin effects, inflammatory mediators, etc., and involving membrane rupture and release of intracellular contents to the surrounding tissue, often with harmful inflammatory consequences. Accordingly, one of the ways in which necrotic cells may be detected and characterized is by detection of compromised cell membranes, e.g. by methods of staining with propidium iodide followed by flow cytometry or microscopy.

SUMMARY OF THE INVENTION

This invention is directed, in part, to the novel and unexpected discovery that administration to a mammal of apoptotic cells and/or apoptotic bodies previously prepared ex vivo, can be used in the prophylaxis and/or treatment of neurodegenerative and/or other neurological disorders in the treated mammal.

Accordingly, in one of its composition aspects, this invention is directed to a pharmaceutical composition comprising a pharmaceutically acceptable excipient and an effective amount of apoptotic cells and/or apoptotic bodies.

The pharmaceutical compositions preferably employ an aqueous based pharmaceutically acceptable excipient although other excipients can be used.

As noted above, these compositions are useful in the prophylaxis and/or treatment of neurodegenerative and/or other neurological disorders in mammals. Accordingly, in one of its method aspects, this invention is directed to a method for the treatment of or prophylaxis against neurodegenerative and other neurological medical disorders in a mammalian patient, which comprises administering to the patient an effective amount of apoptotic bodies and/or apoptotic cells.

These methods are preferably accomplished by administering to the patient the pharmaceutical compositions described herein.

BRIEF DESCRIPTION OF THE DRAWING

The FIGURE is a graph showing a comparison of net ear swelling in mice treated with the compositions of this invention and a control group.

DESCRIPTION OF THE PREFERRED EMBODIMENTS

This invention is directed to the treatment and/or prophylaxis of neurodegenerative and/or other neurological disorders by the administration of apoptotic cells and/or bodies.

Neurodegenerative disorders, including Down's syndrome, Alzheimer's disease and Parkinson's disease, are associated with increased levels of reactive oxygen species (ROS), certain inflammatory cytokines, including interleukin-1β (IL-1β) [see Griffin W S T, Stanley L C, Ling C, White L, Macleod V. Perrot L J, White C L, Araoz C (1989). Brain interleukin 1 and S-100 immunoreactivity are elevated in Down's syndrome and Alzheimer disease. *Proceedings of the National Academy of Sciences USA* 86 7611–7615; Mogi M, Harada M, Narabayashi H, Inagaki H, Minami M, Nagatsu T (1996). Interleukin (IL)-1 beta, IL-1, IL-4, IL-6 and transforming growth factor-alpha levels are elevated in ventricular cerebrospinal fluid in juvenile parkinsonism and Parkinson's disease. *Neuroscience Letters* 211:13–16]. It has also been shown that IL-1β inhibits long-term potentiation in the hippocampus [Murray C A, Lynch M A (1998). Evidence that increase hippocampal expression of the cytokine interleukin-1β is a common trigger for age and stress-induced impairments in long-term potentiation. *Journal of Neuroscience* 18:2974–2981]. Long-term potentiation in the hippocampus is a form of synaptic plasticity and is generally considered to be an appropriate model for memory and learning [Bliss T V P, Collinridge G L, (1993). A synaptic model of memory: long-term potentiation in the hippocampus, *Nature* 361:31–39]. Thus, inappropriate cytokine expression in the brain is currently believed to be involved in the development and progression of neuroinflammatory diseases.

Neurodegenerative and other neurological disorders treatable by the present invention include Down's syndrome, Alzheimer's disease, Parkinson's disease, senile dementia, depression and the like. In summary, it can be substantially any neurodegenerative or other neurological disorder.

"Apoptotic cells" and "apoptotic bodies," as the terms are used herein, means cells and cell bodies which exhibit one or more of the following apoptosis-characterizing features: surface exposure of phosphatidylserine, as detected by standard, accepted methods of detection such as Annexin V staining; alterations in mitochondrial membrane permeability measured by standard, accepted methods (e.g. Salvioli, S., Ardizzoni, A., Franceschi, C. Cossarizza, A. (1997) "JC-1, but not DiOC6(3) or Rhodamine 123, is a Reliable Fluorescent Probe to assess Delta Psi Changes in Intact Cells: Implications for Studies on Mitochondrial Functionality during Apoptosis," *FEBS Letters* 411: 77–82]; evidence of DNA fragmentation such as the appearance of DNA laddering on agarose gel electrophoresis following extraction of DNA from the cells [Teiger, E., Dam, T. V., Richard, L., Wisnewsky, C., Tea, B. S., Gaboury, L., Tremblay, J., Schwartz, K. and Hamet, P. (1996) "Apoptosis in Pressure Overload-induced Heart Hypertrophy in the Rat," *Journal of Clinical Investigation* 97; 2891–2897], or by in situ labeling (see Gavrieli et al., 1992, referenced above).

The apoptotic cells and/or apoptotic bodies for use in the present invention preferably comprise not more than about 35 weight percent of necrotic cells and/or necrotic bodies based on the total weight of the apoptotic cells/bodies and necrotic cells/bodies; more preferably, not more than about 20 weight percent; and even more preferably, not more than about 10 weight percent. At these levels, the presence of such necrotic cells and/or bodies are believed not to significantly alter in vivo processes. In its most preferred embodiment, the apoptotic cells/bodies are substantially free of necrotic cells and or bodies (i.e., less than about 2 weight percent of necrotic cells/bodies).

The apoptotic cells and/or apoptotic bodies for use in the present invention are prepared ex vivo from mammalian cells that are compatible with those of the mammalian patient. They can be prepared from substantially any type of mammalian cell including cultured cell lines. Preferably they are prepared from a cell type derived from the mammalian patient's own body or from an established cell line. More preferably they are prepared from white blood cells of blood compatible with that of the mammalian patient, more preferably from the patient's own white blood cell and even more preferably from the patient's own T lymphocytes. Even more preferably they are prepared from an established cell line. The apoptotic cells and/or apoptotic bodies are prepared extracorporeally prior to administration to the patient. Thus, in one embodiment, an aliquot of the patient's blood may be withdrawn, e.g. by venipuncture, and at least a portion of the white cells thereof subjected extracorporeally to apoptosis inducing conditions.

A variety of methods of inducing apoptosis in mammalian cells, so as to create apoptotic cells and apoptotic bodies, are known in the art and essentially any of these can be adopted in preparing apoptotic bodies for use in the present invention. One such method is the subjection of the cells to ionizing radiation (γ-rays, x-rays, etc.) and/or non-ionizing electromagnetic radiation including ultraviolet light. Apoptosis can be induced by subjecting cells to ultrasound.

Another method is the treatment of the cells with drugs such as non-specific protein kinase inhibitors as exemplified by staurosporine (see Bombeli, Karsan, Tait and Hirlan, (1997) "Apoptotic Vascular Endothelial Cells Become Procoagulant", *Blood,* Vol. 89:2429–2442). Also, certain chemotherapeutic agents used for the treatment of malignant tumours induce apoptosis, for example adriamycin, as can statin drugs (3-hydroxy-3methylglutaryl coenzyme A reductase inhibitors) [Guijarro C, Blanco-Colio L M, Ortego M, Alonso C, Ortiz A, Plaza J J, Diaz C, Hernandez G, Edigo J (1998), "3-hydroxy-3methylglutaryl coenzyme A reductase and isoprenylation inhibitors induce apoptosis of vascular smooth muscle in culture," *Circulation Research* 83:

490–500 and colcicine [Suzuki Y (1998)", "Cell death, phagocytosis and neurogenesis in mouse olfactory epithelium and vomeronasal organ after colcicine treatment, "*Annals of the New York Academy of Sciences* 855: 252–254]. The use of ligands for death receptors on cells, such as Fas-ligand, will be apparent for inducing apoptosis from the discussion of apoptosis above.

Yet another method is the application of oxidative stress to cells extracorporeally (see for example Buttke and Sandstrom (1994) "Oxidative Stress as a Mediator of Apoptosis," *Immunology Today,* Vol. 15:7–10). This can be achieved by treating the cells, in suspension, with chemical oxidizing agents such as hydrogen peroxide, other peroxides and hydroperoxides, ozone, permanganates, periodates, and the like. Biologically acceptable oxidizing agents are preferably used, so as to reduce potential problems associated with residues and contaminations of the apoptotic cells and apoptotic bodies so formed.

The present invention is not restricted to any particular method of producing apoptotic cells and apoptotic bodies, for use herein, and any suitable, known process can be used.

Methods for the detection and quantitation of apoptosis can be used to determine the presence and level of apoptosis in the preparation to be administered to the patient in the present invention. At least one of the methods from those described in the introduction above should be used to confirm the level of apoptosis achieved prior to administration. They are suitably purified prior to use, by methods known in the art, such as differential centrifugation.

In preparing the apoptotic cells and/or apoptotic bodies, care should be taken not to apply excessive levels of oxidative stress, radiation, drug treatment, etc., since otherwise there is a significant risk of causing necrosis of at least some of the cells under treatment. Necrosis causes cell membrane rupture and the release of cellular contents often with biologically harmful results, particularly inflammatory events, so that the presence of necrotic cells and their components along with the apoptotic bodies is best avoided. Appropriate levels of treatment of the cells to create apoptotic bodies for use in the present invention depend to some extent on the nature of the chosen cells and cellular composition, and the type of treatment chosen to induce apoptosis. Such appropriate levels are readily determinable by those skilled in the art, having regard to the available scientific literature on the subject including the above-reference articles.

One preferred process according to the present invention involves the culture of cells from the patient, or a compatible mammalian cell line. The cultured cells may then be treated to induce apoptosis and to create apoptotic cells and/or apoptotic bodies therein. The cells, suspended in the patient's plasma or another suitable suspension medium, such as saline or a balanced mammalian cell culture medium, can then be administered as indicated below. The numbers of apoptotic cells and/or bodies can be determined by published methods available in the scientific literature on the subject including the above-reference articles. The numbers of such apoptotic cells and/or apoptotic bodies required for administration to the patient to obtain the required clinical benefit will vary depending on the source of cells, the patient's condition, the age and weight of the patient and other relevant factors which are readily determinable by the attending clinician.

Thus, an example of a preferred process according to the present invention accordingly involves extraction of an aliquot of blood from the patient to be treated, separation of the white cells therefrom, and treatment of the white cells under apoptosis-causing conditions, so as to create a cellular composition in which significant numbers of the white cells therein have been apoptosed so as to create therein substantial numbers of apoptotic cells or bodies. Then the treated composition is administered to the patient. More preferably, T lymphocytes, isolated from the blood by known means, and suspended as above, may be used as a source of apoptotic cells and apoptotic bodies.

The number of viable cells selected for treatment to create apoptotic cells and/or apoptotic bodies is suitably up to about $4 \times 10^9$, preferably from about 1,000,000 to about 1,000,000,000 and most preferably from about 50,000,000 to about 150,000,000, for each administration to a human patient. From about 10% to 90%, preferably from about 30% to 70% of the cellular composition for administration is comprised of apoptotic bodies and/or apoptotic cells, the balance being viable cells and necrotic cells. Accordingly, the preferred amounts of apoptotic cells and/or apoptotic bodies for administration are those produced by subjecting these numbers of cells to the apoptosing conditions. When whole blood is used as the source of the cells to be subjected to the apoptosis inducing conditions, these numbers of white cells are obtainable in blood aliquots of volume up to about 400 ml, preferably up to 100 ml. More specifically, 50,000,000–150,000,000 cells is equivalent to the white cells in blood aliquots of volume 10–30 ml.

The volume of the aliquot of blood withdrawn from the patient for treatment to create apoptotic cells and/or apoptotic bodies therein is suitable up to about 400 ml, preferably from about 0.1 to about 100 ml and most preferably from about 5 to about 15 ml. Accordingly, the preferred amounts of apoptotic cells and/or apoptotic bodies for administration are those corresponding to the numbers derivable from the white blood cells, or isolated T lymphocytes, contained in such quantities of whole blood, following subjection to apoptosis-inducing conditions.

The suspension of treated apoptotic cells and/or bodies for administration to the patient is prepared in a biologically acceptable liquid suspending medium, such as the patient's serum or plasma, saline or balanced mammalian cell culture medium. The addition of other factors, such as cytokines, hormones, products of stressed cells or other appropriate biologically active material may enhance the benefit of the administered apoptotic cellular materials. The aliquot can be introduced into the patient's body by any suitable method, most preferably intramuscular injection but also including subcutaneous injection, mini-grafting, intra peritoneal injection, intra-arterial injection, intravenous injection and oral administration. The apoptotic entities can be delivered to the specific body organ and/or site by using any appropriate, known delivery system.

The compositions of this invention may optionally include a pharmaceutically acceptable excipient. Some examples of suitable excipients include sterile water, sterile saline, phosphate buffered saline, and the like.

When administered, the pharmaceutical compositions comprise an effective amount of apoptotic bodies/cells to induce a suitable prophylactic and/or therapeutic response in the patient at risk of suffering or suffering from a neurodegenerative disease. Preferably, the composition administered to the mammalian patient comprises from about 10,000 to 10,000,000 apoptotic cells or bodies per kilogram of body weight, more preferably from about 500,000 to 5,000,000 and most preferably from about 1,500,000 to about 4,000,000 apoptotic cells and/or bodies per kg body weight. The specific dose employed will, of course, be dependent upon the age, weight and severity of the disease in the treated patient all of which are within the skill of the attending clinician.

For most effective treatment and/or prophylaxis of mammalian disorders involving a neurodegenerative or neurological disorder, the patient may be given a course of treatments with apoptotic cells and/or bodies according to the invention. Each course of treatment may involve administration to the patient of from 1 to 6 aliquots of suspended cellular material, as described above. No more than one such aliquot should be administered per day, and the maximum rest period between any two consecutive administrations should be not greater than about 21 days. Booster treatments as described below may advantageously be used. To maintain the desired effects, the patient may undergo booster treatments, with a further course of administration of aliquots of suspended apoptotic cells and/or apoptotic bodies as described above, at intervals of three to four months.

As noted, the present invention is applicable to the treatment and prophylaxis of a wide variety of mammalian neurodegenerative and other neurological disorders. These include, but are not limited to, Down's Syndrome, Alzheimer's disease, Parkinson's disease, senile dementia, depression, multiple sclerosis, Huntington's disease, peripheral neuropathies, spinal cord diseases, neuropathic joint diseases, chronic inflammatory demyelinating disease (CIPD), neuropathies including mononeuropathy, polyneuropathy, symmetrical distal sensory neruopathy, cystic fibrosis, neuromuscular junction disorders and myasthenias. In summary, it can be substantially any neurodegenerative or other neurological disorder.

The invention is further described, for illustrative purposes, in the following specific examples.

EXAMPLE 1

Experiments to demonstrate the invention were conducted on laboratory mice, under approved conditions for conducting such experiments.

The effectiveness of the treatment according to a preferred embodiment of the present invention, on contact hypersensitivity (CHS), an example of a Th-1-cell inflammatory disorder which is known to be mediated by inflammatory cytokines, was assessed on laboratory mice, according to approved animal experimentation procedures, using the method described by Kondo et. al., "Lymphocyte function associated antigen-1 (LFA-1) is required for maximum elicitation of allergic contact dematitis" Br. J. Dermatol. 131:354–359 (1994), with minor variations. The disclosure thereof is incorporated herein by reference. Briefly, to induce CHS, the abdominal skin of each mouse was shaved and painted with dinitrodifluorobenzene DNFB, the sensitizing chemical, using 25 µl of 0.5% DNFB in 4:1 acetone: olive oil solution. This sensitization was applied to two groups of Balb/c mice, 10 animals in total.

Apoptotic bodies were prepared from murine fibroblasts. The murine fibroblasts were treated with 50 mM sodium butyrate in RPMI medium, at confluency for one day, and then the sodium butyrate medium was changed. To increase the number of apoptotic cells and bodies, the cells can additionally be irradiated with UV-light (e.g. 75 mj). Supernatant containing floating cells is removed 24 hours following irradiation.

Apoptotic bodies were quantitated by centrifuging the supernatant (1200 rpm, 5 minutes), aspirating the supernatant, washing the resulting cell pellet with PBS and centrifuging again, as above. The pellet containing the apoptotic bodies was re-suspended in PBS. The cells were stored in PBS at 4° C. for the duration of the experiment. The cells to be stained for quantitation were re-suspended in 1× binding buffer at a concentration of $1\times10^6$ cells/ml. 100 µl of the cells were transferred to a 5 ml tube, and 10 µl of fluorescein-conjugated annexin V and 10 µl propidium iodide reagent was added. The cells were gently vortexed and the cell mixture incubated for 15 minutes at 25° C. in the dark. Following the incubation, 400 µl of 1× binding buffer is added to each tube. The sample was analyzed on a flow cytometer over one hour.

Of the two groups of sensitized mice, the first, control group A, received no treatment. The second, test group B, was treated with an injection of suspended apoptotic bodies prepared as described above, 50 µl volume containing at least 150,000 bodies per injection of blood subjected to stressors as described above. Treatments, each involving intramuscular injection of 50 µl of the respective liquid, started on the day of sensitization, and were repeated every day for a total of six days. On the same day as the last treatment, but after its administration, the animals were challenged with DNFB, by applying to the right ear of each animal 10 µl of 0.2% solution of DNFB in acetone and olive oil. To the left ear of each animal was applied the acetone/olive oil solvent, without DNFB. Inflammation due to CHS manifests itself in a swelling of the right ears. Ear thickness was measured, 24 hours after challenge, with a Peacock spring-loaded micrometer (Ozaki Co., Tokyo, Japan). The results were expressed as the thickness and difference in thickness of the right ears and the left ears of each animal, at 24 hours after challenge.

The experiments were repeated, using more sets of two groups of animals, a sufficient number of times to ensure statistical significance in the results. A notable and significant reduction in ear thickness (inflammation) was observed with the animals treated with the apoptotic cells and apoptotic bodies suspension in accordance with the invention, as compared with the untreated group, demonstrating a significant reduction in inflammation. The results are presented in the following Table, and on the accompanying FIGURE, as a bar graph of net ear swelling (difference between right ear and left ear thickness), for each group, with "standard deviation" shown by the vertical line at the top of each column.

TABLE 1

| Group | Left ear | Right ear | Difference |
|---|---|---|---|
| A | 17 | 31 | 14 |
| A | 18 | 39 | 21 |
| A | 17 | 30 | 13 |
| A | 18 | 32 | 14 |
| A | 18 | 31 | 13 |
| | | | Mean: 15 |
| | | | S.D: 3.391165 |
| B | 21 | 31 | 10 |
| B | 18 | 18 | 0 |
| B | 17 | 30 | 13 |
| B | 20 | 24 | 4 |
| B | 18 | 22 | 4 |
| | | | Mean: 6.2 |
| | | | S.D.: 5.215362 |

An analysis of the suspension of apoptotic cells and bodies administered to the animals of test group B indicated the presence therein of approximately 40% apoptotic cells and bodies, balance viable cells and minor amounts of necrotic cells (not more than 20%), the presence of which is believed to be insignificant in the in vivo process.

EXAMPLE 2

The above test procedure was repeated on similar groups of animals, a control group and a test group, but using a suspension of apoptotic cells and bodies on the test group which comprised about 60% apoptotic cells and bodies, balance viable cells and a minor amount (not more than 20%) of necrotic cells. Essentially similar results were obtained.

The effectiveness of the processes and compositions of the present invention in preventing and alleviating inflammation due to CHS indicates that administration of apoptotic cells and bodies as described up-regulates the in vivo generation of anti-inflammatory Th-2 derived cytokines such as IL-10 (known to be implicated in CHS —see Kondo, McKenzie and Sauder, "The Journal of Investigative Dermatology," Vol. 103, 1994, page 811–814) and/or down-regulates Th-1 inflammatory cytokines such as TNFα and IL-6. These inflammatory cytokines are implicated in inflammation-related disorders of the brain, namely the neuroinflammatory, neurodegenerative and neurological disorders such as Alzheimer's disease, senile dementia, multiple sclerosis, depression, Down's syndrome, Huntington's disease, peripheral neuropathies, spinal cord diseases, neuropathic joint diseases, chronic inflammatory demyelinating disease (CIPD), neuropathies including mononeuropathy, polyneuropathy, symmetrical distal sensory neuropathy, cystic fibrosis, neuromuscular junction disorders, myasthenias and Parkinson's disease.

Neurodegenerative diseases, including Down's syndrome, Alzheimer's disease and Parkinson's disease, are associated with increased levels of certain inflammatory cytokines, including interleukin-1β (IL-1β) [see Griffin W S T, Stanley L C, Ling C, White L, Macleod V. Perrot L J, White C L, Araoz C (1989). Brain interleukin 1 and S-100 immunoreactivity are elevated in Down syndrome and Alzheimer disease. *Proceedings of the National Academy of Sciences USA* 867611–7615; Mogi M, Harada M, Narabayashi H, Inagaki H, Minami M, Nagatsu T (1996). Interleukin (IL)-1 beta, IL-1, IL-4, IL-6 and transforming growth factor-alpha levels are elevated in ventricular cerebrospinal fluid in juvenile parkinsonism and Parkinson's disease. *Neuroscience Letters* 211:13–16]. It has also been shown that IL-1β inhibits long-term potentiation in the hippocampus [Murray C A, Lynch M A (1998). Evidence that increase hippocampal expression of the cytokine interleukin-1β is a common trigger for age and stress-induced impairments in long-term potentiation. *Journal of Neuroscience* 18:2974–2981]. Long-term potentiation in the hippocampus is a form of synaptic plasticity and is generally considered to be an appropriate model for memory and learning [Bliss T V P, Collinridge G L, (1993). A synaptic model of memory: long-term potentiation in the hippocampus, *Nature* 361:31–39]. Thus, inappropriate cytokine expression in the brain is currently believed to be involved in the development and progression of neurodegenerative diseases. Consequently, the finding of success in CHS treatment reported in the above Examples, with its attendant down-regulation of Th-1 inflammatory cytokines, is indicative of successful use of the process and compositions in the treatment and prophylaxis of a wide variety of neurological disorders including those discussed above.

What is claimed is:

1. A unit dosage composition for administration to a human patient, comprising a liquid suspension of cellular material including from about 10,000 to 10,000,000 apoptotic cells and/or apoptotic bodies per kilogram of patient body weight, wherein said apoptotic bodies and/or apoptotic cells exhibit at least two characteristics comprising DNA fragmentation, surface exposure of phosphatidylserine, or altered mitochondrial membrane permeability.

2. The unit dosage composition of claim 1, wherein the dosage contains from about 500,000 to about 5,000,000 apoptotic bodies and/or apoptotic cells per kilogram of body weight of said patent.

3. The unit dosage composition of claim 2, wherein the dosage contains from about 1,500,000 to about 4,000,000 apoptotic bodies and/or apoptotic cells per kilogram of body weight of said patent.

4. A unit dosage composition for administration to a human patient, comprising a liquid suspension of cellular material including from about 10,000 to 10,000,000 apoptotic cells and/or apoptotic bodies per kilogram of patient body weight, wherein said apoptotic cells and/or apoptotic bodies exhibit at least two characteristics comprising the binding of Fas ligands to Fas receptors, caspase activation, DNA fragmentation, surface exposure of phosphatidylserine, altered mitochondrial membrane permeability, or release of mitochondrial cytochrome-c.

* * * * *